United States Patent
Papkovsky et al.

(10) Patent No.: US 7,138,270 B2
(45) Date of Patent: Nov. 21, 2006

(54) ASSAY DEVICE AND METHOD FOR CHEMICAL OR BIOLOGICAL SCREENING

(75) Inventors: Dmitri Papkovsky, County Cork (IE); John Charles Alderman, Cork (IE); Rosemary O'Connor, County Cork (IE)

(73) Assignee: University College Cork—National University of Ireland, Cork, Cork (IE)

( * ) Notice: Subject to any disclaimer, the term of this patent is extended or adjusted under 35 U.S.C. 154(b) by 104 days.

(21) Appl. No.: 10/885,079

(22) Filed: Jul. 7, 2004

(65) Prior Publication Data

US 2004/0241783 A1    Dec. 2, 2004

Related U.S. Application Data

(63) Continuation of application No. PCT/IE03/00003, filed on Jan. 16, 2003.

(30) Foreign Application Priority Data

Jan. 17, 2002    (IE)    ................................. 2002/0025

(51) Int. Cl.
*C12M 1/34*    (2006.01)
*C12Q 1/24*    (2006.01)

(52) U.S. Cl. ............................ 435/288.4; 435/305.3; 435/808; 435/33; 422/102; 422/942; 436/165; 359/398

(58) Field of Classification Search ............ 435/305.3, 435/288.4, 808, 33; 422/942; 359/398
See application file for complete search history.

(56) References Cited

U.S. PATENT DOCUMENTS

| | | | |
|---|---|---|---|
| 4,003,707 A | 1/1977 | Lubbers et al. | ............... 23/232 |
| 4,294,924 A | 10/1981 | Pepicelli et al. | ............... 435/30 |
| 4,387,972 A * | 6/1983 | Valencia | ...................... 359/398 |
| 4,599,315 A | 7/1986 | Terasaki et al. | ............ 435/301 |
| 4,657,867 A | 4/1987 | Guhl et al. | .................. 435/284 |
| 4,722,598 A * | 2/1988 | Ford | ........................... 359/398 |
| 4,810,655 A | 3/1989 | Khalil et al. | ................ 436/138 |
| 4,947,850 A | 8/1990 | Vanderkooi et al. | ........ 128/654 |
| 5,155,019 A | 10/1992 | Sussman et al. | .............. 435/34 |
| 5,232,839 A | 8/1993 | Eden et al. | .................... 435/39 |
| 5,371,016 A | 12/1994 | Berndt | ...................... 435/291 |
| 5,770,440 A | 6/1998 | Berndt | ....................... 435/288 |
| 5,792,426 A | 8/1998 | Portmann et al. | ........... 422/102 |
| 6,395,506 B1 * | 5/2002 | Pitner et al. | .................. 435/32 |

FOREIGN PATENT DOCUMENTS

| | | |
|---|---|---|
| DE | 4405375 | 8/1995 |
| DE | 19907011 | 8/2000 |
| EP | 0388159 | 9/1990 |
| GB | 2132348 | 7/1984 |
| WO | WO98/15645 | 4/1998 |
| WO | WO02/25289 | 3/2002 |

* cited by examiner

*Primary Examiner*—William H. Beisner
(74) *Attorney, Agent, or Firm*—Jacobson Holman PLLC (57) ABSTRACT

An assay device (1) comprises a base (2) and glass plate lid (3). The base (2) has an array of shallow microwells (4), each having a flat rim (9), all rims being co-planar. When the lid (3) is placed on the base (2) a thin capillary gap (10) is formed on each rim, acting as a liquid seal for a microwell chamber. The liquid is excess sample liquid and further excess is accommodated in overspill cavities (6) between the microwells (4). Because of the liquid seal and shallow configuration the benefits of microfluidic devices are achieved together with the handling convenience and use of conventional detection equipment of conventional microplate devices.

32 Claims, 4 Drawing Sheets

Comparison of sensitivity (slopes of fluorescent signal) for the respirometric assays of B cells measured in 96 well priorart microplates (■) and in the devices 1 (♦).

Fig. 3

Respiration profiles of a sample containing 300 B cells in one microliter volume and a sample without cells.

Fig. 4

Changes in respiration activity and viability of *S. pombe* cells under the exposure to cadmium nitrate (xenobiotic): concentration and incubation time profiles

Fig. 5

Respiration profiles of surface-attached MCF7 cells (a set of samples) measured with the device. Control samples containing no cells are represented by flat lines

ASSAY DEVICE AND METHOD FOR CHEMICAL OR BIOLOGICAL SCREENING

This is a continuation of PCT/IE03/00003 filed Jan. 16, 2003 and published in English.

FIELD OF THE INVENTION

The invention relates to a device and method for chemical or biological screening of low-volume samples using luminescence detection.

PRIOR ART DISCUSSION

Assessment and characterisation of cell populations, individual cells and their key parameters is very important in multiple research and diagnostic fields. Living cells and their status in terms of viability, differentiation state, growth, or metabolic rate can be assessed by various methods. For example, cells can be stained with vital dyes (for example trypan blue) or labelled antibodies that recognise cell surface markers, followed by quantitation of stained or marked cells by flow cytometry, or qualitative analysis of morphological changes or dye uptake using light or fluorescent microscopy. However, processing of large numbers of cell samples cannot be efficiently or accurately done using microscopy-based methods, or indeed flow cytometric methods.

Cell densitometry enables monitoring of cells on the basis of light scattering, which is proportional to the number of cells in the sample. Cell densitometry (usually absorbance of samples containing cells is monitored at about 600 nm) allows the adaptation of microbiological tests to a micro assay format, for example using standard microtitter plates, and is suitable for high throughput screening applications. To perform densitometry-based analysis of cells relatively large concentrations of cells ($>10^6$–$10^7$ cells/ml), and long assay times (24 h or more, determined by cell division cycle time) are usually required. In addition when small sample volumes are used the sensitivity of cell densitometry is further compromised, due to small optical paths. Some other techniques for example light scattering, allow for non-invasive or minimally-invasive monitoring of living cells, however these techniques are usually costly or inconvenient for use on a large scale.

Various probes, assays and diagnostic systems are available for measuring parameters such as cell growth, viability, drug toxicity or metabolism. Typical examples include: incorporation of radioactively labelled $^3$H-thymidine in cells; MTT colorimetric assay of mitochondrial respiration via the formation of coloured product (formazan); fluorimetric assays for cell membrane integrity and permeability (e.g. using Calcein-AM dye); fluorescent probes for intracellular $Ca^{2+}$; various enzymatic and receptor based assays (see e.g. Handbook of Fluorescent Probes and Research Chemicals, Molecular Probes Inc., 1996). These assays are used in combination with a microscope, spectrometer, or fluorescence-based plate reader. However, most of these cell-monitoring assays have major limitations in that they employ probes that bind to or have to be loaded into the cells, so that after such assays cells do not remain intact. This often entails removing the cells from culture medium to buffers that can alter their characteristics and results in making the analysis of cell function less accurate or representative of the conditions that are under investigation. Furthermore, these assays are usually multi-step, time-consuming and employ only end-point detection possibilities and require a set of standards.

Metabolic activity tests are also used to determine the status of micro-organisms, their growth, viability and other characteristics in response to various stimuli or environmental conditions. Such tests are not directly related to the cell division cycle time and therefore in many cases can be performed faster. Cell metabolic activity tests become useful when large numbers of samples are to be processed and/or evaluated comparatively.

Living cells and micro-organisms can be detected by measuring ATP as a marker of metabolism via bioluminescence. This approach, however, usually requires sampling of the cultures and further extensive treatment of the samples to extract ATP, and therefore is not very suitable for continuous monitoring or for high throughput screening applications. A method for monitoring of biological activity is described based on the infrared detection of carbon dioxide in the gaseous atmosphere above the medium of sealed samples (M. Sussman et al, U.S. Pat. No. 5,155,019). This method however, is not very sensitive and difficult to use with small sample volumes and for measurement of low levels of respiration. It is also particularly unsuitable for many cultured mammalian cells that use $CO_2$ to buffer the growth medium.

Oxygen is one of the key metabolites which can be used for the detection of living cells, their respiration and growth rates, as well as other biological and chemical processes associated with oxygen consumption or release. Monitoring of the dissolved oxygen uptake comprises a simple and convenient way for the evaluation of metabolic activity for many micro-organisms, and also for mammalian cells. Since oxygen diffusion in aqueous solutions is fast and it freely penetrates cell membranes and whole cells, monitoring of oxygen uptake by biological samples can be carried out non-invasively, i.e. outside the cells. On the other hand, the use of oxygen consumption or release by a biological sample as an indicator of metabolic activity and growth of living micro-organisms is usually complicated by the vast excess of oxygen in the environment.

Oxygen consumption in biological samples can be quantified by measuring pressure change in the headspace of samples placed in closed test-vials containing built-in pressure sensors (U.S. Pat. No. 5,232,839). This method is not very accurate, is time-consuming due to the high oxygen capacity of test vials (headspace). It is costly, and it is difficult to apply the method to very small sample volumes. It is also limited by the number of available test vials and pressure sensors, and is therefore not suitable for high throughput screening applications.

Dissolved oxygen can also be monitored with the electrochemical oxygen sensor—Clark-type oxygen electrode. The electrode, however, consumes oxygen and it usually requires stirring and/or control of mass-exchange conditions in a sample. It is not suitable for measurements that do not involve contact with the sample. It requires frequent recalibrations. It can be poisoned by certain chemical species and it is difficult to sterilise.

Fluorescent detection techniques usually provide a high degree of sensitivity and selectivity. Molecular oxygen is known as a quencher of fluorescent molecules, and can be quantified by quenching of fluorescence (U.S. Pat. No. 4,003,707). Long-lived luminescent dyes, particularly fluorescent complexes of ruthenium(II) (GB2132348) and phosphorescent platinum(II) and palladium(II) complexes of porphyrins (U.S. Pat. Nos. 4,810,655, 4,947,850), are the most common dyes for the development of optical sensors for oxygen. To produce an oxygen probe, the dye is usually embedded in an appropriate polymer matrix and applied as a coating onto a solid substrate such as a glass slide, plastic foil or optical fibre. When the sensor is placed in contact with the sample or near the sample, oxygen from the sample penetrates the coating and quenches the emission of the dye. By measuring luminescent signal from the sensor, one can quantify oxygen concentration in a sample using a predetermined relationship, i.e. calibration. Fluorescence-based monitoring of oxygen provides high sensitivity and imaging capabilities, and the possibility to work on a micro-scale. It also enables a contact-less sensing of oxygen in a sample, as only optical contact between the sensor and fluorescent detector is needed.

WO98/15645 describes a microbiological method whereby a biological sample containing living micro-organisms was assessed by measuring gradients of the dissolved oxygen, using a solid-state luminescence-based oxygen sensor and a special set-up for measurement. The system, however, requires a complicated measurement cell chamber to isolate the sample from ambient air and a special design of the oxygen sensor active element. U.S. Pat. No. 5,371,016 describes a method for detecting biological activities in a plurality of culture vials that employs a solid-state fluorescent oxygen probe spread along the inner surface of sealable containers. U.S. Pat. No. 5,770,440 describes an apparatus for early detection of micro-organisms for analysing a plurality of partial samples using a CCD camera. Each sample has its own headspace and its own oxygen sensor. The Oxygen Biosensor System from Becton Dickinson also uses a solid-state fluorescent oxygen probe permanently attached to the bottom of a microwell plate.

These methods are not optimal for measurement of small oxygen gradients, small numbers of slowly respiring cells, small sample volumes and large numbers of samples. These methods are usually based on the measurement of local oxygen gradients using solid-state oxygen probes which require additional preparation steps, for example coating steps. The existing systems also have problems associated with the presence of vast amount of oxygen in ambient air, from which test samples are not isolated in an effective and convenient way. Flow-through devices (e.g. microfluidics in glass or plastic substrates) can solve the problem of a tight air seal, but they are not very practical for HTS applications, problematic for use with attachment cells, and can be relatively costly. In addition, the incorporation of solid-state oxygen-sensitive coatings in such systems increase their costs with some waste of materials and make miniaturisation more difficult.

SUMMARY OF THE INVENTION

According to the invention, there is provided an assay device comprising a base and a lid, wherein,
the base comprises a plurality of wells each having a wall, and an overspill cavity between the wells,
each well wall has a rim, and
the well rims and the lid comprise means for forming a capillary gap suitable to retain excess liquid sample forming a seal around each well.

In one embodiment, the rim width is in the range of 0.2 mm to 3.0 mm.

In another embodiment, the well width is in the range of 1.0 mm to 10 mm and the depth is in the range of 10 µm to 1000 µm.

In a further embodiment, the rims are co-planar.

In one embodiment, the base further comprises a frame configured to form an outer barrier with the lid for a plurality of wells.

In another embodiment, there are a plurality of frames, each for a sub-set of the wells.

In a further embodiment, the overspill cavities are bounded by the outer surfaces of the wells and the frame.

In one embodiment, the frame comprises a vent for ambient air or gas escape during placement of the lid on the base.

In another embodiment, the frame and the rims are co-planar.

In a further embodiment, the lid comprises a glass plate.

In one embodiment, the wells are of circular configuration having annular walls.

In another embodiment, the base and the lid are of any one or more of silicon, plastics, ceramics, or glass.

In a further embodiment, the plastics material is selected from any one of polyester, polyamide, polyvinyl chloride, or polymethyl metacrylate.

In one embodiment, the base is of injection moulded material.

In another embodiment, the base is of embossed material.

In a further embodiment, the lid and/or the base are optically transparent to allow optical inspection of samples when the lid is on the base.

In one embodiment, an inner surface of at least one well is coated with a luminescent probe.

In another embodiment, the probe is of luminescent solid-state dye-polymer composition.

In a further embodiment, the inner surface of at least one well is pre-treated for selective adhesion or growth of test cells.

In one embodiment, the device comprises formations to allow gripping by robotic handling equipment.

According to another aspect, the invention provides a method for analysing liquid samples, the method comprising the steps of:
depositing the samples in wells of an assay device as defined above, whereby each sample volume is greater than the final volume of the well when the lid is in place;
providing a luminescent probe in the sample or in the device;
placing the lid onto the base so that excess sample in each well forms a film in a capillary gap between the rim of its well and the lid to form a microwell chamber with a liquid seal;
operating a detection system to monitor luminescence of the probe in each well over a period of time; and
determining a parameter of the sample according to change of luminescence with time.

In one embodiment, the volume of sample placed in each well is sufficient to overspill into the overspill cavity and there is continuity between the sample enclosed in the wells, that on the rim, and that in the overspill cavity.

In another embodiment, the device is handled as a unit in a manner in which the lid is secured to the base by liquid thin film attraction of the base to the lid.

In a further embodiment, the method comprises the step of maintaining the device at an optimal temperature prior to sealing the samples in the microwells.

In one embodiment, the probe comprises a long-decay oxygen-sensitive luminescent dye selected from the following group: fluorescent complexes of ruthenium(II) or osmium(II), phosphorescent platinum(II)- or palladium(II)-porphyrins, or close analogs or derivatives thereof.

In another embodiment, the probe comprises a solid-state coating.

In a further embodiment, the probe is water-soluble.

In one embodiment, the probe is an oxygen probe and comprises a conjugate of the phosphorescent Pt-porphyrin dye with a hydrophilic macromolecule such as protein.

In another embodiment, the samples are pre-mixed with the water-soluble oxygen probe prior to adding the samples to the microwells.

In a further embodiment, the luminescent signal from the probe is measured by time-resolved or phase-resolved fluorescence.

In one embodiment, oxygen uptake by the samples is determined on the basis of changes of the luminescence lifetime of the probe.

In another embodiment, oxygen uptake by the samples is determined on the basis of changes of the luminescence phase shift of the probe.

In a further embodiment, the sample comprises living cells or micro-organisms.

In one embodiment, the microwell depth is larger but comparable with the size of the cells or micro-organisms.

In another embodiment, the sample comprises sub-cellular fragments such as microsomes, mitochondria, or cellular extracts.

In a further embodiment, the samples comprise an oxygen-dependent enzyme or enzymatic system such as glucose oxidase, xanthine oxidase, lactate oxidase, ethanol oxidase, cytochrome P450 family.

In one embodiment, the method is for use in determining the effect on living cells of effectors such as drugs, toxicants, proteins or DNA.

In another embodiment, the method is for use in the determination of the metabolism or viability of cells in response to different stimuli such as hormones or stress.

DETAILED DESCRIPTION OF THE INVENTION

BRIEF DESCRIPTION OF THE DRAWINGS

The invention will be more clearly understood from the following description of some embodiments thereof given by way of example only with reference to the accompanying drawings, in which.

DETAILED DESCRIPTION OF THE EMBODIMENTS

Figure 1:
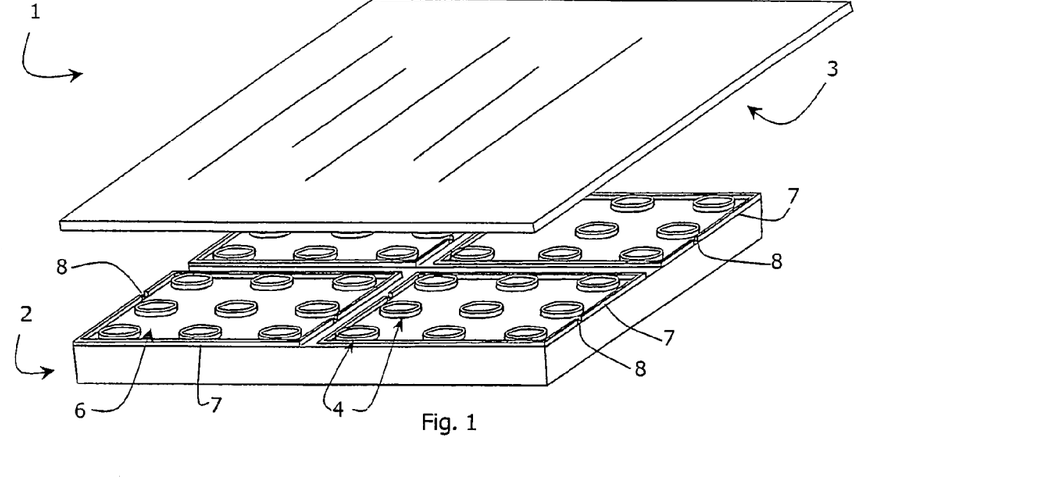
FIG. 1 is a perspective view of an assay device of the invention.
Figure 2A:
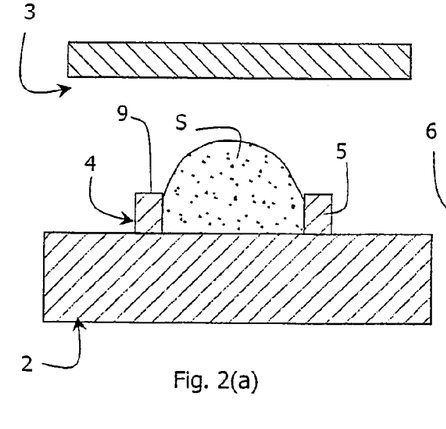
FIG. 2 is a diagrammatic cross-sectional view illustrating operation of the device.
Figure 2B:
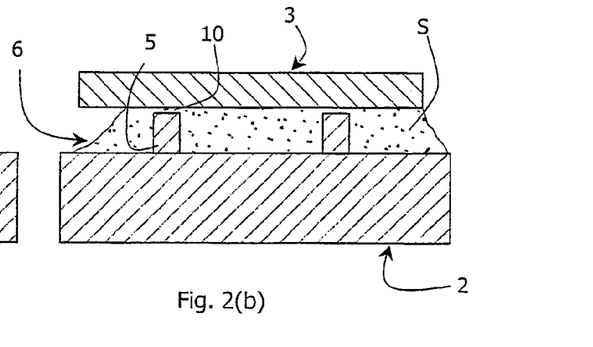

Referring to FIGS. 1, 2(a), and 2(b) an assay device 1 of the invention comprises a base 2 and a lid 3. The base 2 comprises microwells 4 each of circular shape in plan and having a wall 5. There are overspill cavities or areas 6 on the base 2 between the microwells 4. The base 2 further comprises peripheral walls forming frames 7 around each group of nine microwells 4. Each frame 7 comprises a vent 8. The base 2 is of silicon material, and the lid 3 is a flat glass plate, in this embodiment a conventional glass slide. The tops, 9, of the microwell walls 5 are co-planar and are flat. They act as a rim for sealing with the lid 3 to form a microwell chamber in use and are henceforth referred to as rims.

The base 2 is made using a standard 4-inch silicon wafer as a substrate. Using a photopolymerisation chemistry (SU-8 monomer) process, the surface of the wafer is profiled to produce the microwells 5, the over-spill cavities 6, and the frames 7 of the desired size and shape. The device 1 comprises 4×9 microwells, with the locations of the microwells corresponding to those of a conventional 96-well plate. The device 1 may therefore be easily aligned on the platforms of conventional fluorescence plate readers either alone or alongside other devices. The size of the microwells is approximately 4 mm in diameter, with a wall 5 thickness of approximately 1.0 mm and height of approximately 60 μm. There is a 9 mm pitch between the microwells. The frames 7 surrounding the microwells 4 are co-planar with the mircrowells 4 and have a width of 1 mm.

In use, referring to particularly FIGS. 2(a) and 2(b) a test sample S is placed in each microwell 4 with a volume of 2.5 μl, exceeding the height of the walls 5. The lid 3 is then placed over the base 2 so that it lies uniformly over all of the walls 5 and the frames 7.

As the lid 3 is placed on the base, excess sample S overspills into the surrounding overspill areas 6. As shown most clearly in FIG. 2(b) a residual amount of sample S fills a capillary gap 10 between the rim 9 and the lid 3. For clarity, the size of the gap 10 has been exaggerated in FIG. 2(b). Therefore, the desired volume of the sample S is completely surrounded by the base 2 and the lid 3 without any ambient air contact. The excess sample S is on the rim 9 forming the microchamber seal, and in the overspill cavities 6. Contact of the lid 3 and the frames 7 forms a second level of enclosure, also limiting access by ambient air and minimising sample evaporation and contamination. The vents 8 ensure uniform placement of the lid 3 by allowing ambient air to escape as the overspill cavities 6 receive excess sample S during placement of the lid 3.

When the lid 3 is in place the fact that the microwells 4 and the cavities 6 are shallow means that the liquid sample is in a thin film. Surface tension and atmospheric pressure then help to keep the lid and the base together, for easy manipulation as a unit.

The device allows simple, rapid, and sensitive assessment of chemical or biological samples such as populations of living cells on the basis of detecting the oxygen consumption or release from cells. It is particularly suited for the analysis of large numbers of samples and screening applications because in plan view it has the same general arrangement of wells as conventional assay devices. This allows it to be used with conventional sample deposition and optical detection equipment. It essentially achieves the low-volume and accuracy of microfluidic assay devices with the convenience of conventional devices.

The device provides for the detection of relatively small levels of uptake/release of compounds such as oxygen in test samples, and small changes in the level of uptake/release and/or small cell numbers. The device effectively excludes ambient air from the sample, and minimises the diffusion of oxygen to and from the sample during the measurement of oxygen levels in the sample, thus making the assay more sensitive and reliable.

The efficiency of the seal of the microwell chambers formed by the base and the lid is determined by a number of parameters including the diameter of the microwells, wall thickness, the depth and volumes of the microwells and overspill cavities, the device material, and also by sample volume. Too large or too small a sample volume can result in flooding the device and/or an improper seal, or leave air bubbles in the microwells. An incompletely full microwell can compromise the device performance. All these parameters are optimised in the device to provide optimal performance in respirometric assays.

The microwells 4 are designed to allow the detection of minor levels of oxygen uptake or release in biological samples under investigation. They have relatively small depth and a large surface area. The rim width is preferably in the range of 0.2 to 3.0 mm, the microwell depth is preferably in the range of 10 microns to 1000 microns, and the microwell diameter is preferably in the range of 1 mm to 10 mm.

This geometry facilitates optical measurement, easy sample handling and easy growing of cells in the microwells 4 if necessary, while at the same time minimising the consumption of biological and other reagents used. For the sensitive measurement of respiration of cells, the microwell depth is usually comparable with the size of test cells, of the order of 30 to 500 microns. The device design also makes it easier to dispense biological samples into the microwells, grow the cells in the microwells, manipulate the biological samples and measure fluorescence from the oxygen probe.

The luminescent oxygen probe used in conjunction with the device and with an external detector system to monitor oxygen uptake/release by biological samples may be a solid-state probe or water-soluble probe. The probe may be, admixed with each biological sample and/or dispensed to the microwells during the preparation steps of the assay before the device is sealed. In one example the probe is an oxygen probe, and is henceforth referred to as such.

The oxygen probes may for example be those based on the phosphorescent porphyrins, or fluorescent complexes of ruthenium(II) and osmium(II), or close analogs or derivatives of these dyes. In one embodiment the probe comprises a luminescent oxygen-sensitive polymer coating which is applied on the inner surface of the microwells 4. Preferably the phosphorescent dye(s) for such oxygen probes are selected from any one or more of Pt-tetraphenylporphine, Pt-tetrakis(pentafluorophenyl)porphine, Pt-octaethylporphyrin, Pt-octaethylporphine-ketone, Pt-coproporphyrin-I tetramethyl ester, Pd-octaethylporphyrin, Pd-tetrakis(pentafluorophenyl) porphine, Pd-tetraphenyl-porphine, Pd-benzoporphine, Pd-octaethylporphine-ketone.

The solid-state oxygen probe may be applied to the bottoms of the microwells or to the lid, so that after the device assembly it is located in the sides of the microchambers and exposed to the samples. Various luminescent oxygen-sensitive compositions commonly used in oxygen sensors may be used for the coating of the microwells. Examples of such coatings include platinum(II)-octaethylporphine-ketone in polycarbonate or polysulfone; ruthenium(II)-diphenylphenantroline adsorbed on silicagel particles and embedded in silicon rubber, ruthenium(II)-diphenylphenantroline in polystyrene; platinum(II)-tetrakis (pentafluoro-phenyl)porphine in polystyrene. Coatings having small intrinsic capacity for oxygen are preferred. Coating of the device with the solid-state oxygen probe can be carried out using a "cocktail" of the probe components in appropriated organic solvent.

In another embodiment of the invention the oxygen probe is water-soluble. Preferred water-soluble oxygen probes are those based on the phosphorescent dyes. The dye(s) for such oxygen probes are selected preferably from any one or more of the following dyes: Pt-coproporphyrin, Pt-tetrakis(p-carboxyphenyl)porphine, Pt-tetrakis(p-sulfophenyl)porphine Pt-coproporphyrin-ketone, Pd-coproporphyrin, Pd-tetrakis (p-carboxyphenyl)porphine, Pd-coproporphyrin-ketone, or close analogs and derivatives of these dyes.

Preferably the water-soluble oxygen probe comprises a conjugate of the phosphorescent dye with a hydrophilic macromolecule such as protein. Examples of the water-soluble oxygen probe include, for example, platinum(II)-coproporphyrin-I conjugated to serum albumin.

The use of water-soluble oxygen probes generally facilitates easy preparation of the devices and samples, and execution of the assays. Using water-soluble oxygen probes added to the samples just before the assay is carried out can also minimise the toxic effects of the probe on test cells such as phototoxicity and continuous exposure for example.

Pre-coating of the device may be also carried out by applying an aqueous solution of the water-soluble oxygen probe to these areas and allowing it to dry. Upon addition of liquid sample, the probe readily dissolves in it. Pre-coating may also be achieved by passive adsorption of water-soluble oxygen probe, similar to the well-known ELISA. In this case, the oxygen probe stays adsorbed during the assays and gives luminescent response to oxygen concentration changes in the sample.

The physical-chemical properties of the oxygen probe are important, especially when analysing samples containing living cells. Preferred oxygen probes for the assay device are cell-impermeable probes and those having low chemical, photo- and cytotoxicity. Spectral characteristics of the luminescent oxygen probe are important when performing the respirometric screening assay of samples, particularly for biological samples and samples containing living cells. Such samples may have complex optical properties and autofluorescence which can cause interference in screening assays. The use of longwave and long-decay oxygen probes on the basis of phosphorescent platinum(II) and palladium(II)-porphyrins in combination with time-resolved phosphorescence detection allow to minimise optical interferences. The use of luminescence lifetime-based sensing of oxygen rather than intensity-based sensing is also preferred, as this can minimise errors due to variation in probe concentration and static quenching. Luminescence lifetime-based sensing is usually achieved by time-domain measurements, or by phase-modulation techniques. The time-resolved luminescence detection lifetime-based oxygen sensing are the preferred detection methods for the respirometric assays of this invention. For example, measurement of long-lived emission of the oxygen probe at several delay times after excitation eliminates background interference and allows the measurement of the emission with high sensitivity and the calculation of the lifetime and correlate it with the oxygen concentration.

The screening method employs kinetic monitoring of the luminescence of the oxygen probe in each microwell chamber. If sample temperature is maintained constant, changes in luminescence over time reflect the changes in the dissolved oxygen concentration. An increase in luminescence intensity and lifetime of the probe indicates the consumption of oxygen by the sample, whereas a decrease in these parameters indicates the release of oxygen.

By measuring the intensity, lifetime, or phase characteristics of the luminescence of the oxygen probe, the oxygen concentration and oxygen gradient in a sample is determined using a known relationship.

To determine oxygen gradients in the microwell chambers comprising biological samples, the luminescence is measured at different time intervals to determine changes in luminescence parameters. This is achieved by periodic measurement of the luminescence in each microwell chamber and plotting time profiles, by two-point measurement at two time points (for example zero point and end-point) and determining the slope, or by continuous monitoring of each sample sequentially or in parallel. This may be carried out using conventional fluorescence plate readers, imagers or dedicated instruments.

The rates of oxygen uptake or release by a sample under particular conditions measured by means of oxygen probes and quenched-luminescence oxygen sensing, is a good indication of the metabolic status or biological activity of the sample. In most cases, the method operates with samples which are initially in gas equilibrium with ambient air, before they are sealed in the microwell chambers of the device of the invention. For example, for pure water at 20° C. and normal atmospheric pressure, this would correspond to the dissolved oxygen concentration of about 200 micromoles/l.

The measurement of absolute concentrations of dissolved oxygen and the rates of oxygen uptake or release by test samples is usually not necessary, and relative values and scales may be used instead. In this case, time profiles of luminescence, initial slopes or threshold levels of the luminescence intensity, lifetime or phase shift, can be used to assess the respiration activity of samples with respect to a reference sample or standard.

The device of the invention may be used at elevated or at low temperatures. For example, experiments with living cells are usually carried out at temperatures around 30° C. to 37° C. Fast and uniform temperature control is achieved because of the large device surface area in contact with the liquid sample.

The experimental time period can vary from a few minutes up to several hours. It is therefore important that good equilibration of the temperature of samples is carried out in order to maintain samples at optimal conditions and to be able to measure small changes in the dissolved oxygen concentration. Materials such as silicon which have good heat conductivity and which can provide rapid temperature equilibration of the device and uniform temperature of all samples within device are preferred. However, other materials such as plastics (e.g. PET, PMMA) or glass may be used. Materials which have low permeability to gases such as oxygen are preferred.

Using the devices of this invention, respirometric measurements of biological samples comprising cells usually require relatively short periods of time than other devices based on similar detection principles.

A biological screening method using the device of the invention comprises the following steps:

preparing the device, oxygen probe and samples under investigation for the respirometric assay, treating the samples with various drugs or effectors if necessary;

placing the samples in individual microwells of the device together with the oxygen probe, in volumes exceeding the final volume of the microwell chambers;

assembling the device to remove air and excess sample from the microwells, create uniform microwell chambers, sealed with excess of sample liquid on the rims 9 and essentially protected from interference by ambient oxygen;

monitoring of luminescence of the oxygen probe in each microwell chamber over a period of time to establish the changes in luminescent signal reflecting the oxygen gradients; and correlating the oxygen gradients or changes in luminescent signal over time with biological or chemical parameters of test samples or changes of these parameters.

The preparation of the biological samples for the respirometric assay, particularly samples comprising cells, may include growing test cells under appropriate conditions with different medium, nutrients, temperature, pH or gases. A preliminary assessment by chemical or biological tests such as counting of cell numbers may be necessary to perform basic characterisation of the samples under investigation. The samples may be treated by the addition of effectors and other additives prior to the assay.

In the case of screening of drug candidates and other effectors which are expected to have chemical or biological effects on test samples or cells, a plurality of samples are treated with such compounds under appropriate conditions, dose, and timescale. The treated samples are then added to the microwells to evaluate the biological or chemical effect on the samples by measuring the rates of their oxygen uptake or release. A reference or a set of references such as untreated samples is used as controls.

Biological samples are placed in the microwells by simple dispensing methods. Adherent cells which require attachment to the surface for their normal functioning and growth may be grown directly in the microwells of the device, or on the lid. The treatment of biological samples may be carried out while the samples are in the microwells. Some additional accessory tools and/or procedures such as treatment of surfaces may be required to treat the biological samples and grow cells in the device.

The sample volume required for the respirometric assay should exceed that of the microwell chamber. The optimal volume or volume range is determined by the profiled surface of the device, its material and the sample properties. The assay therefore allows flexibility with sample volume, and compensation for inaccurate dispensing and evaporation of small volumes. At the same time, if sample volume is too large the device can become flooded and seal efficiency compromised. Typically a volume of at least 110% is preferred. The upper limit is set by the capacity of the overspill cavities 6.

The device and method operate with shallow microchambers (typically 30–200 microns deep), as opposed to conventional microplates (2–10 mm deep). The resultant short optical path and small sample volume impose additional requirements/restrictions for the luminescent probe and detection system used. These requirement are satisfied by the probes giving strong luminescent signals, having long-wave (visible) excitation and emission bands and long lifetimes, such as Pt-porphyrin base probes. Time-resolved luminescent detection provides further enhancement of the screening performance, by reducing optical background originating from the sample and device material, by providing a high signal to noise ratio, and reduced probe consumption.

Coating of the microwells with a solid-state probes can be difficult, due to the small size of the wells. Considerable thickness of such coating (usually micron range, i.e. comparable with the depth of microwells) and intrinsic capacity for oxygen, adhesion to the base, edge effects, the danger of contamination of the rim during deposition procedure, etc. may create additional difficulties and compromise the device performance and sealing efficiency. Therefore, the use of water-soluble oxygen probes is a preferred option.

The invention will be more clearly understood from the following examples.

EXAMPLE 1

Using the Device for Monitoring Cellular Respiration

Three milligrams of platinum(II)-coproporphyrin-I (PtCP) was dissolved in 0.1 ml of dimethylformamide, mixed with 1 mg of 1-ethyl-3-(3-dimethylaminopropyl) carbodiimide in 0.1 ml dimethylformamide and incubated for 10 minutes at room temperature. The solution was added dropwise to 3 ml of solution of bovine serum albumin (BSA, 2 mg/ml) in 0.1M carbonate buffer, pH9.0 and incubated at room temperature to allow the dye derivative to react with protein amino groups. The covalent conjugate PtCP-BSA formed was purified from the excess of unbound dye by chromatography on a desalting column in phosphate buffer saline, collecting the fractions of PtCP-BSA conjugate. The concentration for the PtCP-BSA conjugate stock was determined spectrophotometrically. This stock solution of the oxygen probe was added to the samples to achieve the desired working concentration. Such samples can undergo respirometric measurements in the microwells of the device as described below.

Figure 3:
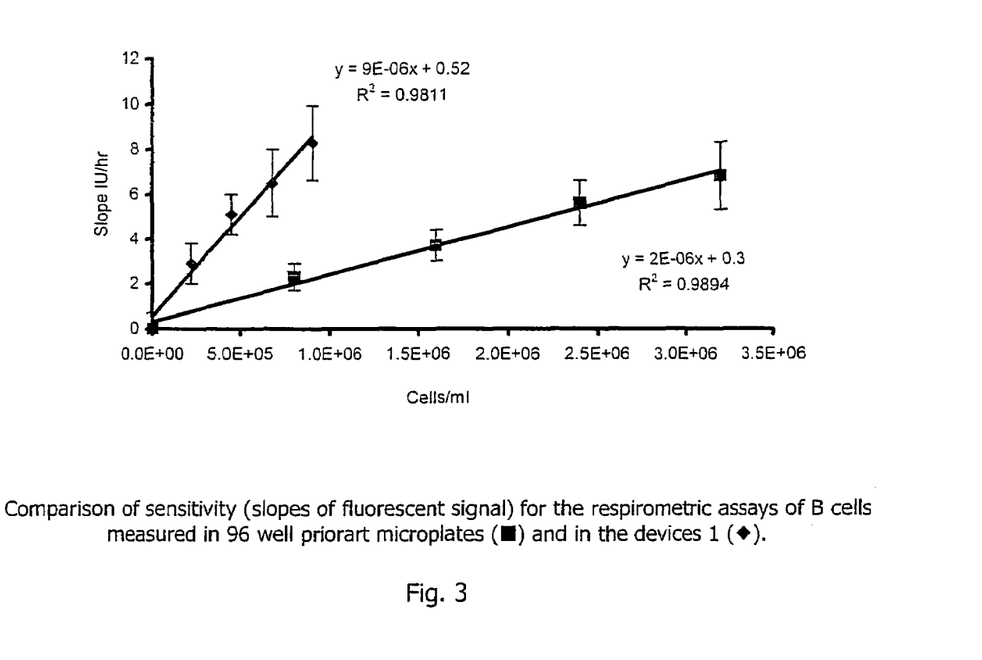
FIG. 3 is a plot illustrating a comparison of sensitivity of the device with prior art microplates.
Figure 4:
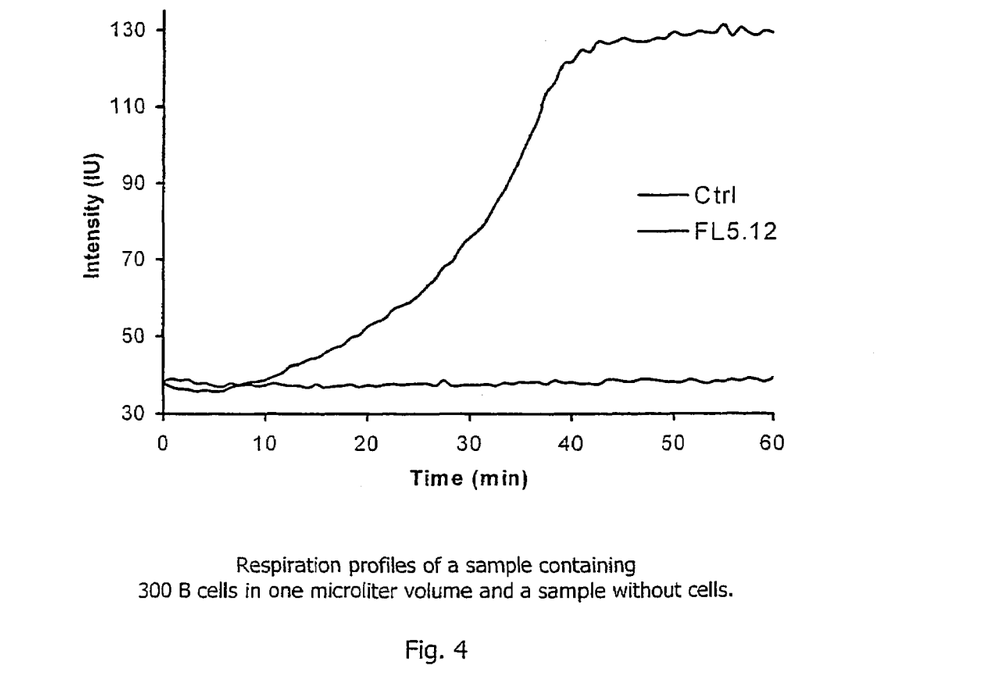
FIG. 4 is a graph showing the respiration profile of B-lymphocytes compared to a control sample with no cells present.

To a suspension of live human non-activated B lymphocytes ($3 \times 10^6$ cells/ml) prepared by cellular fractionation and immunomagnetic bead separation of the whole blood, the PtCP-BSA probe was added at a final concentration of $3 \times 10^{-5}$M. Two microlitres of this suspension was added to the microwells of the device 1. The samples were sealed using a cover glass. The device was placed on a metal plate positioned in the microplate compartment of a fluorescence plate reader SpectraMax Gemini (Molecular Devices) and equilibrated at 37° C. The phosphorescent signal in each well was monitored using excitation at 380 nm and detection at 650 nm. Comparative tests with a conventional microplate device and a planar glass slide comprising microwells were also carried out and results are shown in FIG. 3. A typical respiration profile for a sample containing small number of freshly isolated B cells is shown in FIG. 4, in comparison to a control sample comprising medium without cells.

EXAMPLE 2

Using the Device for Measurement of Oxygen Uptake in an Enzymatic Reaction

Two microlitres of a solution containing 0.5 ug/ml of glucose oxidase enzyme, 10 mM of β,D-glucose and $3*10^{-5}$ M of PtCP-BSA probe prepared as described in Example 1 above in 0.1 M phosphate buffer, pH6.0 was aliquoted into each microwell of the device. The microwells were then sealed with the glass lid 3 placed in a plate reader SpectraMax Gemini (Molecular Devices), equilibrated at 37° C. and the phosphorescent signal in each well was monitored. Phosphorescence was monitored at 650 nm using excitation at 380 nm. As in the Example 1, the device 1 demonstrates superior performance requiring less sample and showing greater sensitivity within a shorter time period, when compared to the assays performed in standard microplates.

EXAMPLE 3

Assessment of Viability of Cultured Yeast Cells B Treated with Toxicant

A solid-state oxygen probe comprising a thin film polymer coating of the phosphorescent dye platinum(II)-tetrakis (pentafluorophenyl)porphine (PtTFPP) and polycarbonate was used with the device 1 shown in FIG. 1. One milligram of PtTFPP is dissolved in 0.01% (w/v) solution of polycarbonate (M.ca. 60 000) in chloroform. One microlitre aliquotes of this solution were dispensed to the microwells and allowed to air dry for 10 minutes to produce thin film phosphorescent oxygen-sensitive coating inside the microwells.

Figure 5:
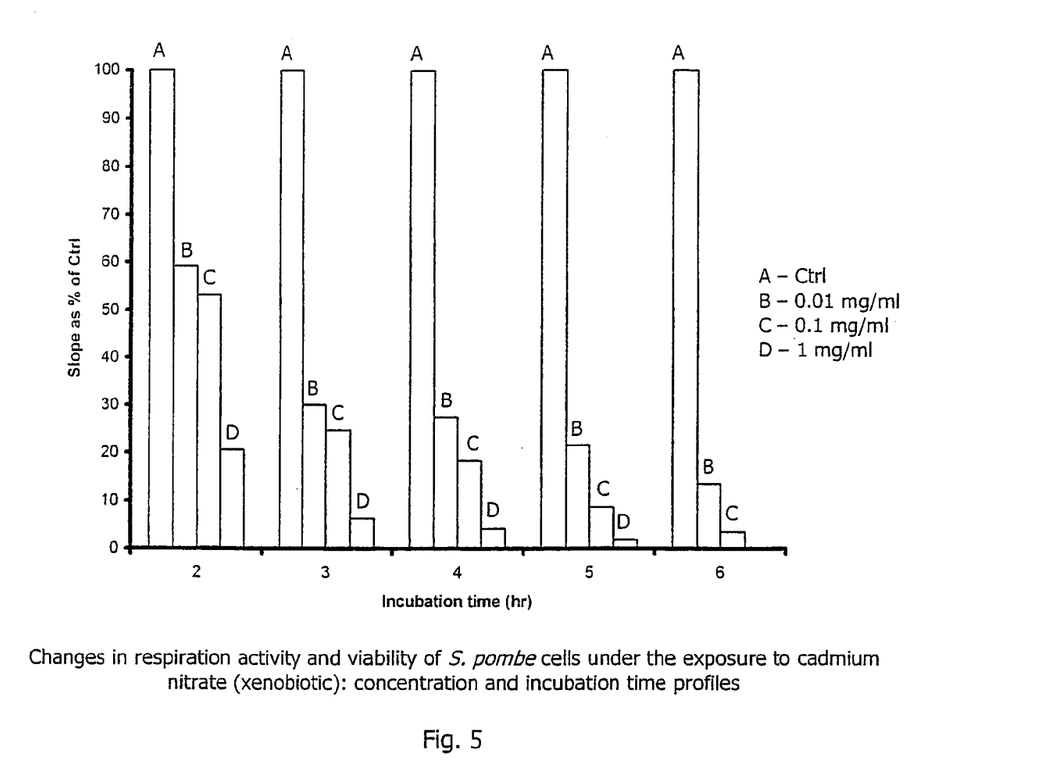
FIG. 5 is a bar chart showing changes in respiration activity and viability of S. pombe cells under the exposure to cadmium nitrate (xenobiotic) (concentration and incubation time profiles)

*S. pombe* yeast cells were incubated with different concentrations of cadmium nitrate toxicant. Two μl aliquots were taken from each sample at different time intervals, and placed in the wells of microwell chambers coated with a PtTFPP-polycarbonate solid-state oxygen probe. The respiration profiles of samples were monitored as described in Example 1 above, together with a control sample containing the same concentration of test cells, but without the presence of a toxicant. The levels of oxygen uptake by each sample is evaluated on the basis of time profiles of the phosphorescent signal (initial slopes), compared to those obtained in the control sample. A decrease in the initial slope and oxygen uptake with respect to control sample indicated the changes in cell viability as shown in FIG. 5. This could be extended to compare cells growing in the presence of necessary growth factors, undergoing survival factor deprivation, or undergoing apoptosis.

EXAMPLE 4

Monitoring of Respiration of Mammalian MCF7 Adherent Cells

Figure 6:
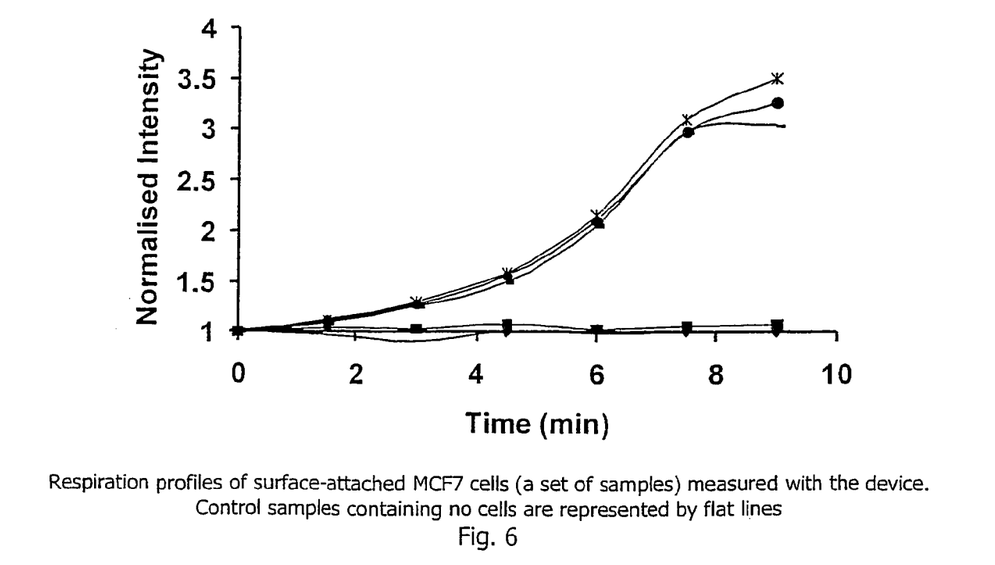
FIG. 6 is a plot showing monitoring of respiration of surface attached cells.

Breast carcinoma MCF-7 cell line was maintained in Dulbecco's modified Eagle's medium supplemented with 10% fetal calf serum, 10 mM glucose and 5 mg/ml penicillin/streptomycin. After 24 hours in culture the cells were plated on glass slides at concentration of $7 \times 10^5$ per ml and cultured for an additional 16 hours. Slides were removed from culture and excess fluid was removed. Aliquotes of PtCP-BSA (3.5 μl $1 \times 10^{-5}$ M in DMEM) were spotted onto the low volume assay platform. The platform was then covered with the glass slide, aligned on a metal plate (125×85×10 mm) which was then inserted in a standard fluorescence plate reader SpectraMax Gemini (Molecular Devices), equilibrated at 37° C. The phosphorescent signal in each well was monitored at 650 nm using excitation at 380 nm. Results shown in FIG. 6 demonstrate fast and reproducible response of the cells in the device. The MCF7 cells grown in standard 96-well plates in the same conditions did not produce measurable oxygen gradients, due to small cell numbers and low respiration rates.

It will be appreciated that the invention provides an optimised microwell device, for the analysis of a range of small chemical or biological samples, in conjunction with a luminescent oxygen probe and an external fluorescence detector such as a standard fluorescence plate reader. It provides for contact-less and non-invasive assessment of different biological samples. In particular it provides for the assessment of small numbers of slowly respiring cells such as mammalian cells, in a simple and cost-effective manner using simple reagents, measurement instrumentation and accessories. A number of samples may be monitored at the same time and the device provides an effective seal for the samples in the microwell chambers so that ambient oxygen is effectively excluded and small levels of oxygen uptake/release by test cells and small oxygen gradients can be detected reliably. The method is based on an integrated and self-contained device, which allows easy handling and operation of the device itself and also test samples used in it.

A screening method using the device provides significantly increased assay sensitivity. It allows for the rapid determination of small cell numbers. Very small oxygen gradients may be monitored using the device with conventional detection equipment. This is achieved without the need for microfluidic devices, which are expensive, complex, and difficult to use. The device and method of the invention also provide for the possibility to reuse test sample cells after the respirometric assay has been carried out so that the same cell samples may be used in other assays. This is particularly important in applications where there are only a small number of cells available for testing.

Cell-respirometric assays according to this invention can be coupled with other cell-based assays which also employ optical detection systems for example fluorescence, chemiluminescence, absorbance, and corresponding probes and other reagents. Very distinct spectral and decay characteristics of the oxygen probes used in this invention allow their selective and sensitive detection in the presence of other fluors with minimal or no cross-sensitivity, thus allowing multiplexed assays. Examples include staining of cells with dyes (trypan blue), fluorescence based assays for membrane integrity, LDH, intracellular calcium, etc. Such probes and assays are generally compatible with the oxygen probes and cell-respirometric assays and can be combined together to allow multiplexing.

The method also provides for the screening of large numbers of samples which may have been treated in different ways with for example effectors such as chemicals, toxicants, proteins, polysaccharides, nucleic acids, microorganisms, cells, mixtures and complex samples, for example.

The device has potential application in areas such as cell viability assays, cell growth and proliferation assays, drug screening, effector action, monitoring single cells, simple organisms, microbes, bacteria, enzymatic reactions and other processes associated with oxygen uptake or release.

The invention is applicable to monitoring of gas analytes other than oxygen in biological and chemical samples, including $CO_2$, $NH_3$, NO, $SO_2$, $CH_4$ and other gas and volatiles compounds, using appropriated optical detection systems and/or probes.

Figure 7:
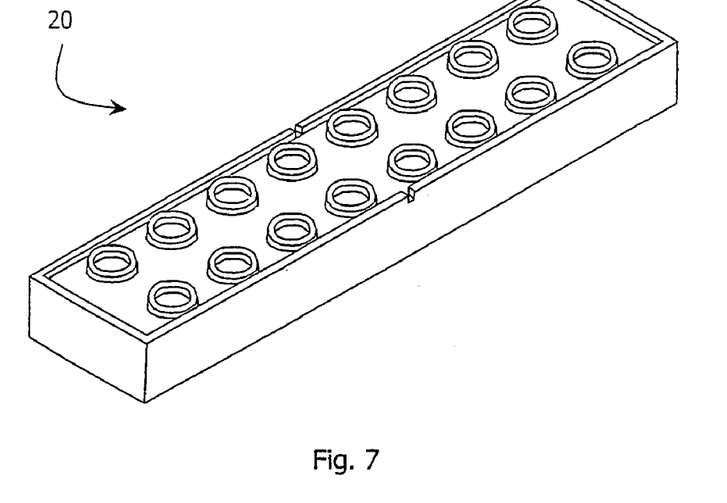
FIGS. 7 and 8 are perspective views of alternative assay devices of the invention.
Figure 8:
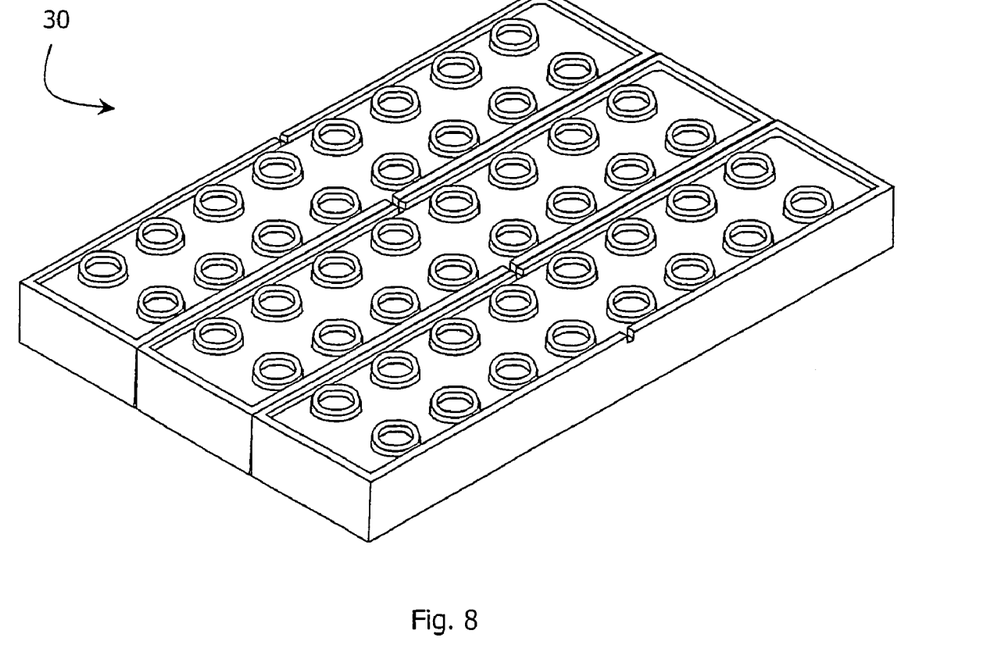

The invention is not limited to the embodiments hereinbefore described which may be varied in construction and detail. The overall device configuration may vary, depending on the application. In other embodiments, the microwells may be of approximately 2 to 3 mm in diameter; be 30, 100 or 150 µm deep, and have a wall thickness of 0.1, 0.2, or 0.5 mm, for example. There may be a higher density of microwells such as a 384-well format. Two alternative devices 20 and 30 are shown in FIGS. 7 and 8 respectively. The device 20 comprises a 2×8 microwell elementary unit mimicking 96-well strips. Its key elements (base, microwells, walls, cavities, frames and valves) are the same as in FIG. 1. A standard glass cover slide 1"×3" is used as a lid. The device 30 is an assembly of three of the units 20 to give an analog of a half 96-well plate (same footprint, 9 mm pitch between all wells) or sections of the microplate. In another alternative, the device may have the overall configuration of an optical disc, and it may be produced using a variation of optical disc production techniques. In this embodiment, the microwells would have a circular alignment and there may be a single circular frame or multiple concentric frames or a continuous helical frame. Also, the base (i.e. the profiled part having the microwells) may overlie the lid (i.e. flat part). Alternatively, both parts may be profiled.

Alternatively, the overspill cavities may be at a lower level than the bases of the microwells to provide greater capacity. Also, the device base and/or lid may alternatively be mass-produced from any of a wide variety of plastics materials using moulding, embossing, or lithographic techniques.

The invention claimed is:

1. An assay device comprising a base and a lid, wherein,
    the base comprises a plurality of wells each having a wall, and an overspill cavity between the wells,
    each well wall has a rim,
    the well rims and the lid comprise means for forming a capillary gap suitable to retain excess liquid sample forming a seal around each well,
    the lid comprises a flat plate and the well rims are co-planar;
    the rim width is in the range of 0.2 mm to 3.0 mm;
    the well width is in the range of 1.00 mm to 10 mm, and the depth is in the range of 10 µm to 1,000 µm; and
    the base further comprises a frame configured to form an outer barrier with the lid and surrounding a plurality of wells, the overspill cavities are bounded by the outer surfaces of the wells and by the frame, and the frame and the rims are co-planar.

2. The assay device as claimed in claim 1, wherein there are a plurality of frames, each for a sub-set of the wells.

3. The assay device as claimed in claim 1, wherein the frame comprises a vent for ambient air or gas escape during placement of the lid on the base.

4. The assay device as claimed in claim 1, wherein the lid comprises a glass plate.

5. The assay device as claimed in claim 1, wherein the wells are of circular configuration having annular walls.

6. The assay device as claimed in claim 1, wherein the base and the lid are of any one or more of silicon, plastics, ceramics, or glass.

7. The assay device as claimed in claim 6, wherein the plastics material is selected from any one of polyester, polyamide, polyvinyl chloride, or polymethyl metacrylate.

8. The assay device as claimed in claim 1, wherein the base is of injection moulded material.

9. The assay device as claimed in claim 1, wherein the base is of embossed material.

10. The assay device as claimed in claim 1, wherein the lid and/or the base are optically transparent to allow optical inspection of samples when the lid is on the base.

11. The assay device as claimed in claim 1, wherein an inner surface of at least one well is coated with a luminescent probe.

12. The assay device as claimed in claim 11, wherein the probe is of luminescent solid-state dye-polymer composition.

13. The assay device as claimed in claim 1, wherein the inner surface of at least one well is pre-treated for selective adhesion or growth of test cells.

14. The assay device as claimed in claim 1, wherein the device comprises formations to allow gripping by robotic handling equipment.

15. A method for analysing liquid samples, the method comprising the steps of:
- depositing the samples in wells of an assay device as claimed in claim 1, whereby each sample volume is greater than the final volume of the well when the lid is in place;
- providing a luminescent probe in the sample or in the device;
- placing the lid onto the base so that excess sample in each well forms a film in a capillary gap between the rim of its well and the lid to form a microwell chamber with a liquid seal in which the volume of sample in the well is free of ambient air contact;
- operating a detection system to monitor luminescence of the probe in each well over a period of time; and
- determining a parameter of the sample according to change of luminescence with time.

16. The method as claimed in claim 15, wherein the volume of sample placed in each well is sufficient to overspill into the overspill cavity and there is continuity between the sample enclosed in the wells, that on the rim, and that in the overspill cavity.

17. The method as claimed in claim 15, wherein the device is handled as a unit in a manner in which the lid is secured to the base by liquid thin film attraction of the base to the lid.

18. The method as claimed in claim 15, comprising the step of maintaining the device at an optimal temperature prior to sealing the samples in the microwells.

19. The method as claimed in claim 15, wherein the probe comprises a long-decay oxygen-sensitive luminescent dye selected from the following group: fluorescent complexes of ruthenium(II) or osmium(II), phosphorescent platinum(II)- or palladium(II)-porphyrins, or close analogs or derivatives thereof.

20. The method as claimed in claim 15, wherein the probe comprises a solid-state coating.

21. The method as claimed in claim 15, wherein the probe is water-soluble.

22. The method as claimed in claim 21, wherein the probe is an oxygen probe and comprises a conjugate of the phosphorescent Pt-porphyrin dye with a protein or other hydrophilic macromolecule.

23. The method as claimed in claim 21, wherein the samples are pre-mixed with the water-soluble oxygen probe prior to adding the samples to the microwells.

24. The method as claimed in claim 15, wherein the luminescent signal from the probe is measured by time-resolved or phase-resolved fluorescence.

25. The method as claimed in claim 24, wherein oxygen uptake by the samples is determined on the basis of changes of the luminescence lifetime of the probe.

26. The method as claimed in claim 25, wherein oxygen uptake by the samples is determined on the basis of changes of the luminescence phase shift of the probe.

27. The method as claimed in claim 15, wherein the sample comprises living cells or micro-organisms.

28. The method as claimed in claim 27, wherein the microwell depth is larger but comparable with the size of the cells or micro-organisms.

29. The method as claimed in claim 15, wherein the sample comprises microsomes, mitochondria, cellular extracts or other sub-cellular fragments.

30. The method as claimed in claim 15, wherein the samples comprise glucose oxidase, xanthine oxidase, lactate oxidase, ethanol oxidase, cytochrome P450 family or other oxygen-dependent enzyme or enzymatic system.

31. The method as claimed in claim 15, for use in determining the effect on living cells of drugs, toxicants, proteins, DNA or other effectors.

32. The method as claimed in claim 15, for use in the determination of the metabolism or viability of cells in response to hormones, stress or other stimuli.

* * * * *